United States Patent
Knauf et al.

(10) Patent No.: US 10,626,078 B2
(45) Date of Patent: *Apr. 21, 2020

(54) METHOD OF PRODUCING DIAMINES AND POLYAMINES OF THE DIPHENYLMETHANE SERIES AT DIFFERENT PRODUCTION CAPACITIES

(71) Applicant: COVESTRO DEUTSCHLAND AG, Leverkusen (DE)

(72) Inventors: Thomas Knauf, Dormagen (DE); Stefan Wershofen, Mönchengladbach (DE); Klaus-Gerd Gruner, Duisburg (DE); Volker Hartjes, Duisburg (DE)

(73) Assignee: Covestro Deutschland AG, Leverkusen (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/470,300

(22) PCT Filed: Dec. 18, 2017

(86) PCT No.: PCT/EP2017/083257
§ 371 (c)(1),
(2) Date: Jun. 17, 2019

(87) PCT Pub. No.: WO2018/114765
PCT Pub. Date: Jun. 28, 2018

(65) Prior Publication Data
US 2020/0087244 A1    Mar. 19, 2020

(30) Foreign Application Priority Data
Dec. 22, 2016   (EP) .................................. 16206117

(51) Int. Cl.
C07C 209/78    (2006.01)
C07C 209/54    (2006.01)
(Continued)

(52) U.S. Cl.
CPC .......... *C07C 209/78* (2013.01); *C07C 209/54* (2013.01); *C07C 209/60* (2013.01); *C07C 211/48* (2013.01); *C07C 211/50* (2013.01)

(58) Field of Classification Search
None
See application file for complete search history.

(56) References Cited

U.S. PATENT DOCUMENTS

| | | |
|---|---|---|
| 5,053,539 A | 10/1991 | Yano et al. |
| 5,286,760 A | 2/1994 | Bolton et al. |

(Continued)

FOREIGN PATENT DOCUMENTS

| | | |
|---|---|---|
| DE | 844896 C | 9/1952 |
| EP | 1616890 A1 | 1/2006 |

(Continued)

OTHER PUBLICATIONS

International Search Report, PCT/EP2017/083257, dated Apr. 10, 2018. Fritz, Martin.

(Continued)

*Primary Examiner* — Clinton A Brooks
(74) *Attorney, Agent, or Firm* — Donald R. Palladino (57) ABSTRACT

The invention relates to a method for producing diamines and polyamines of the diphenylmethane series, by condensing aniline and formaldehyde followed by an acid-catalysed rearrangement at different production capacities. By adapting the temperatures in the acid-catalysed rearrangement step, the rearrangement reaction can be fully completed despite the change in dwell time inevitably associated with changed production capacity, with no undesired changes occurring in the product composition.

11 Claims, 3 Drawing Sheets

(51) Int. Cl.
 *C07C 209/60* (2006.01)
 *C07C 211/48* (2006.01)
 *C07C 211/50* (2006.01)

(56) References Cited

U.S. PATENT DOCUMENTS

| | | |
|---|---|---|
| 6,433,219 B1 | 8/2002 | Strofer et al. |
| 6,576,788 B1 | 6/2003 | Penzel et al. |
| 6,649,798 B2 | 11/2003 | Klein et al. |
| 7,186,857 B2 | 3/2007 | Muller et al. |
| 7,253,321 B2 | 8/2007 | Hagen et al. |
| 7,312,362 B2 | 12/2007 | Keggenhoff et al. |
| 7,528,283 B2 | 5/2009 | Pohl et al. |
| 9,701,617 B2 | 7/2017 | Wershofen et al. |
| 9,815,769 B2 | 11/2017 | Knauf et al. |
| 10,125,090 B2 | 11/2018 | Knauf et al. |
| 10,125,091 B2 | 11/2018 | Knauf et al. |
| 2017/0137367 A1 | 5/2017 | Knauf et al. |

FOREIGN PATENT DOCUMENTS

| | | | |
|---|---|---|---|
| GB | 1517585 A | 10/1975 | |
| WO | 2014173856 A1 | 10/2014 | |
| WO | 2015197519 A1 | 12/2015 | |
| WO | 2015197520 A1 | 12/2015 | |
| WO | 2015197527 A1 | 12/2015 | |
| WO | WO2018114763 | * 6/2018 | ........... C07C 209/78 |

OTHER PUBLICATIONS

Twitchett, H.J., Chemistry of the production of organic isocyanates, Chem. Soc. Rev. 3(2), 223, 1974.

Mass-Transfer Operations, 3rd ed., 1980, p. 477-541, McGraw-Hill Book Company.

Mueller, E. et al., Liquid-Liquid Extraction, Ullmann's Encyclopedia of Industrial Chemistry, vol. 21, 2012, p. 272-274, Wiley-VCH Verlag GmbH & Co. KGaG.

Mixer-Settler Cascades or Settling Vessels, Kirk-Othmer Encyclopedia of Chemical Technology, Jun. 15, 2007, p. 22-23.

* cited by examiner

METHOD OF PRODUCING DIAMINES AND POLYAMINES OF THE DIPHENYLMETHANE SERIES AT DIFFERENT PRODUCTION CAPACITIES

CROSS-REFERENCE TO RELATED APPLICATION

This application is a national stage application under 35 U.S.C. § 371 of PCT/EP2017/083257, filed Dec. 18, 2017, which claims the benefit of European Application No. 16206117.0, filed Dec. 22, 2016, both of which are incorporated by reference herein.

FIELD

The present invention relates to a process for preparing di- and polyamines of the diphenylmethane series by condensation of aniline and formaldehyde followed by acid-catalyzed rearrangement at different production capacities. Adjusting the temperatures in the acid-catalyzed rearrangement step achieves running of the rearrangement reaction to completion in spite of the change in residence time inevitably associated with the altered production capacity and avoiding any unwanted changes in the product composition.

BACKGROUND

The preparation of di- and polyamines of the diphenylmethane series (MDA) by reaction of aniline with formaldehyde in the presence of acidic catalysts is known in principle. In the context of the present invention, di- and polyamines of the diphenylmethane series are understood to mean amines and mixtures of amines of the following type:

(I)

n here is a natural number ≥2. The compounds of this type in which n=2 are referred to hereinafter as diamines of the diphenylmethane series or diaminodiphenylmethanes (MMDA hereinafter; "monomer MDA"). Compounds of this type in which n>2 are referred to in the context of this invention as polyamines of the diphenylmethane series or polyphenylene polymethylene polyamines (PMDA hereinafter; "polymer MDA"). Mixtures of the two types are referred to as di- and polyamines of the diphenylmethane series (for the sake of simplicity referred to hereinafter as MDA). The corresponding isocyanates that can be derived in a formal sense by replacing all $NH_2$ groups with NCO groups from the compounds of the formula (I) are accordingly referred to as diisocyanates of the diphenylmethane series (MMDI hereinafter), polyisocyanates of the diphenylmethane series or polyphenylene polymethylene polyisocyanates (PMDI hereinafter) or di- and polyisocyanates of the diphenylmethane series (MDI hereinafter). The higher homologs (n>2), both in the case of the amine and in the case of the isocyanate, are generally always present in a mixture with the dimers (n=2), and so only two product types are of relevance in practice, the pure dimers (MMDA/MMDI) and the mixture of dimers and higher homologs (MDA/MDI).

The position of the amino groups on the two phenylene groups in the dimers (para-para; ortho-para and ortho-ortho) is specified hereinafter only when it is important. For the sake of simplicity, this is done in the X,Y'-MDA form (4,4'-, 2,4'- or 2,2'-MDA), as is customary in the literature. The same is true of MDI (identification of the isomers as X,Y'-MDI (4,4'-, 2,4'- or 2,2'-MDI).

Industrially, the di- and polyamine mixtures are converted predominantly by phosgenation to the corresponding di- and polyisocyanates of the diphenylmethane series.

The continuous or partly discontinuous preparation of MDA is disclosed, for example, in EP-A-1 616 890, U.S. Pat. No. 5,286,760, EP-A-0 451 442 and WO-A-99/40059. The acidic condensation of aromatic amines and formaldehyde to give di- and polyamines of the diphenylmethane series proceeds in multiple reaction steps. In what is called the "aminal process", in the absence of an acidic catalyst, formaldehyde is first condensed with aniline to give what is called aminal, with elimination of water. This is followed by the acid-catalyzed rearrangement to MDA in a first step to give para- or ortho-aminobenzylaniline. The aminobenzylanilines are converted to MDA in a second step. Main products of the acid-catalyzed reaction of aniline and formaldehyde are the diamine 4,4'-MDA, its positional isomers 2,4'-MDA and 2,2'-MDA and the higher homologs (PMDA) of the various diamines. In what is called the "neutralization process", aniline and formaldehyde are converted in the presence of an acidic catalyst directly to aminobenzylanilines, which are then rearranged further to give the bicyclic MMDA isomers and higher polycyclic PMDA homologs. The present invention relates to the aminal process.

Irrespective of the process variant for preparation of the acidic reaction mixture, the workup thereof, according to the prior art, is initiated by neutralization with a base. This neutralization is typically effected at temperatures of, for example, 90° C. to 100° C. without addition of further substances (cf. H. J. Twitchett, Chem. Soc. Rev. 3(2), 223 (1974)). It can alternatively be effected at a different temperature level in order, for example, to accelerate the degradation of troublesome by-products. Hydroxides of the alkali metal and alkaline earth metal elements are suitable as bases. Preference is given to using sodium hydroxide solution.

After the neutralization, the organic phase is separated from the aqueous phase in a separating vessel. The organic phase which comprises crude MDA and remains after removal of the aqueous phase is subjected to further workup steps, for example washing with water (base washing) in order to wash residual salts out of the crude MDA. Finally, the crude MDA thus purified is freed of excess aniline, water and other substances present in the mixture (e.g. solvents) by suitable methods, for example distillation, extraction or crystallization. The workup which is customary according to the prior art is disclosed, for example, in EP-A-1 652 835, page 3 line 58 to page 4 line 13, or EP-A-2 103 595, page 5 lines 21 to 37.

International patent application WO 2014/173856 A1 provides a process for preparing di- and polyamines of the diphenylmethane series by converting aniline and formaldehyde in the absence of an acidic catalyst to aminal and water, removing the aqueous phase and processing the organic aminal phase further to give the di- and polyamines of the diphenylmethane series, in which use of a coalescence aid in the phase separation of the process product obtained in the aminal reaction reduces the proportion of water and hence also of water-soluble impurities in the organic phase comprising the aminal. The di- and polyamines of the diphenylmethane series that are obtained by acid-catalyzed rearrangement and workup after further processing of the aminal phase are of excellent suitability for preparation of the corresponding isocyanates.

The quality of a reaction process for preparation of MDA is defined firstly by the content of unwanted secondary components and impurities in the crude product that can arise from improper conduct of the reaction. Secondly, the quality of a reaction process is defined in that the entire process can be operated without technical production outage or problems that necessitate intervention in the process, and that losses of feedstocks are prevented or at least minimized.

Although the prior art processes described succeed in preparing MDA with a high yield and without loss of quality in the end products, the only processes described are in the normal state of operation. Only a few publications are concerned with states outside normal operation:

International patent application WO 2015/197527 A1 relates to a process for preparing di- and polyamines of the diphenylmethane series (MDA), to a plant for preparation of MDA and to a method of operating a plant for preparation of MDA. The invention enables optimization of production shutdowns in the operation of the MDA process with regard to time taken and optionally also with regard to energy and material consumption by means of what is called a circulation mode in individual plant components. During an interruption in the process or interruption of the operation of individual plant components, there is no introduction of formaldehyde into the reaction, and the plant components that are not affected by an inspection, repair or cleaning measure are operated in what is called circulation mode. What this achieves, among other effects, is that only the plant component in question must be shut down for the period of the measure, which may be advantageous in terms of productivity and economic viability of the process and the quality of the products prepared.

International patent application WO 2015/197519 A1 relates to a process for preparing diamines and polyamines of the diphenylmethane series, in which care is taken during the running-down of the production process that an excess of aniline over formalin is ensured.

International patent application WO 2015/197520 A1 relates to a process for preparing diamines and polyamines of the diphenylmethane series (MDA) from aniline and formaldehyde, in which care is taken during the start-up procedure to ensure that there is a sufficient excess of aniline over formaldehyde which is at least 105% of the molar ratio of aniline to formaldehyde wanted for the target formulation of the MDA to be produced.

Changes in the target production capacity (also called "change in load") during continuous production (i.e. with a starting state and an end state, in which MDA is produced) are not taken into account here either. Since aniline is typically used in stoichiometric excess, the production capacity of a given plant for preparation of MDA is defined by the formaldehyde feed which, in the context of this invention, is referred to as (formaldehyde) load.

Changes in load are recurrent plant states that have a considerable effect on the economic (and environmentally benign in terms of energy consumption) operation of a continuously operating plant. Since, for a given continuous production plant, a change in load is inevitably associated with a change in the residence time of the reaction mixture in the reaction space available, as well as purely economic, environmental and operational challenges, there may additionally be an unwanted change in the composition of the product. The exact composition of the MDA obtained (especially the isomer ratio of MMDA and the ratio of MMDA to PMDA) is also crucially dependent on the residence time of the reaction mixture, and so, in the event of improper procedure, a significantly different product can be obtained after a change in load, even though this was not intended.

It would thus be desirable to have available a process for preparing di- and polyamines of the diphenylmethane series in which it is possible by simple measures to configure changes in load in the operation of the MDA process such that these run in an optimized manner (for instance with regard to yield, time taken, energy consumption and avoidance of process-related problems such as caking or blockages in apparatus) in economic, environmental and operational aspects with avoidance of unwanted changes in the product composition.

SUMMARY

According to the invention, this can be accomplished by a process according to patent claim 1. This process, as will be elucidated in detail hereinafter, is more particularly characterized in that the temperature in at least one of the rearrangement reactors is increased in the event of an intended increase in load and is lowered in the event of an intended decrease in load.

All configurations of the present invention relate to a process for preparing di- and polyamines of the diphenylmethane series from aniline (1) and formaldehyde (2) in a production plant (10 000), where the molar ratio of total aniline used (1) to total formaldehyde used (2), n(1)/n(2), is always greater than 1.6, comprising the steps of:

(A-I) reacting aniline (1) and formaldehyde (2) in the absence of an acidic catalyst in a reactor (1000, aminal reactor) to obtain a reaction mixture (4) comprising an aminal (3), and then at least partly separating an aqueous phase (6) from the reaction mixture (4) in a removal unit (2000, also called aminal separator) to obtain an organic phase (5) comprising the aminal (3);

(A-II) contacting the organic phase (5) which comprises the aminal and is obtained in step (A-I) with an acidic catalyst (7) in a reactor cascade (3000) composed of i reactors connected in series (3000-1, 3000-2, . . . , 3000-i), where i is a natural number from 2 to 10 (acid-catalyzed rearrangement), wherein the first reactor (3000-1) in flow direction is operated at a temperature $T_{3000-1}$ in the range from 25.0° C. to 65.0° C., preferably in the range from 30.0° C. to 60.0° C., and is charged with stream (5) and acidic catalyst (7) and optionally with further aniline (1) and/or further formaldehyde (2), every reactor downstream in flow direction (3000-2, . . . , 3000-i) is operated at a temperature of more than 2.0° C. above $T_{3000-1}$ and is charged with the reaction mixture obtained in the reactor immediately upstream;

(B) isolating the di- and polyamines of the diphenylmethane series from the reaction mixture (8-i) obtained from step (A-II) in the last reactor (3000-i) by at least (B-I) adding a stoichiometric excess of base (9), based on the total amount of acidic catalyst used (7), to the reaction mixture (8-i) obtained in the last reactor (3000-i) in step (A-II) in a neutralization unit (4000, preferably stirred neutralization vessel) to obtain a reaction mixture (10), especially observing a molar ratio of base (9) to total acidic catalyst used (7) in the range from 1.01 to 1.30 (neutralization);

(B-II) separating the reaction mixture (10) obtained in step (B-I) in a separation unit (5000, neutralization separator) into an organic phase (11) comprising di- and polyamines of the diphenylmethane series and an aqueous phase (12).

The expressions "total aniline used" and "total formaldehyde used" each refer to the total amount of these reactants used in the process according to the invention, i.e. including any proportions additionally added after step (A-I).

BRIEF DESCRIPTION OF THE DRAWINGS

Various features and characteristics of the inventions described in this specification may be better understood by reference to the accompanying figures, in which.

DETAILED DESCRIPTION

The organic phase (11) can, as described in detail hereinafter, be subjected to further workup. According to the invention, the abovementioned steps are conducted continuously, meaning that the respective reactants are supplied continuously to the apparatus assigned to the respective step and the products are withdrawn continuously therefrom.

In the event of a change in load in the context of the invention, a significant change in the product composition is unwanted, meaning that changes in the product composition are to be largely avoided. What is meant in the context of the present invention by changes in the product composition being largely avoided through the change in load is particularly characterized in that the ratio of total aniline used to total formaldehyde used (n(1)/n(2) hereinafter; also referred to as A/F ratio in the literature) is essentially the same before and after the change in load, wherein slightly greater deviations from the n(1)/n(2) ratio before the change in load can be permitted during the change in load, which makes the change in load more easily controllable in terms of control technology.

According to the invention—in simplified terms; details are elucidated further down—the procedure is thus that, in the event of a change in load, the molar ratio of total acidic catalyst used to total aniline used (n(7)/n(1) hereinafter; also referred to as protonation level=n(7)/n(1)·100%) is kept essentially constant and the temperature in at least one of the reactors 3000-2, . . . , 3000-$i$ is adjusted such that, in spite of an altered residence time, the rearrangement reaction proceeds to completion and unwanted changes in the product composition as a consequence of the change in load are largely avoided. According to the invention, the n(7)/n(1) ratio after the change in load is essentially the same as before the change in load, wherein slightly greater deviations from the n(7)/n(1) ratio before the change in load can be permitted during the change in load. Because both the n(1)/n(2) ratio and the n(7)/n(1) ratio are subject to small deviations at most at any time in the course of a change in load, the aniline (1), formaldehyde (2) and acidic catalyst (7) feedstocks are essentially simultaneously reduced (reduction in load) or increased (increase in load). The slightly greater tolerances in the n(1)/n(2) ratio and n(7)/n(1) ratio during the change in load allow easier control over the change in load in terms of control technology. The tolerances permitted in accordance with the invention, which are still to be elucidated in detail further down, however, are still within such a scope that operational problems are largely to completely avoided.

This procedure allows advantageous configuration of changes in load in economic, environmental (from the point of view of energy consumption) and operational aspects.

Since the invention relates to changes in load, i.e. to different states of operation of a production plant, the following definitions of terms that are used hereinafter are helpful:

Starting state A of the production plant with a given production capacity defined by the amount of formaldehyde introduced:

mass flow rate $m_1$ of total aniline used in the starting state: $m_1(A) \neq 0$ [e.g. in t/h], mass flow rate $m_2$ of total formaldehyde used in the starting state: $m_2(A) \neq 0$ [e.g. in t/h], mass flow rate $m_7$ of total acidic catalyst used in the starting state: $m_7(A) \neq 0$ [e.g. in t/h], molar ratio n(1)/n(2) of total aniline used (1) to total formaldehyde used (2) in the starting state: n(1)/n(2)(A) and molar ratio n(7)/n(1) of total acidic catalyst used to total aniline used in the starting state: n(7)/n(1)(A).

End state E of the production plant with a target production capacity defined by the amount of formaldehyde introduced (with introduction of less or more formaldehyde compared to the starting state):

mass flow rate $m_1$ of total aniline used in the end state: $m_1(E) \neq 0$ [e.g. in t/h], mass flow rate $m_2$ of total formaldehyde used in the end state: $m_2(E) \neq 0$ [e.g. in t/h], mass flow rate $m_7$ of total acidic catalyst used in the end state: $m_7(E) \neq 0$ [e.g. in t/h], molar ratio n(1)/n(2) of total aniline used (1) to total formaldehyde used (2) in the end state: n(1)/n(2)(E) and molar ratio n(7)/n(1) of total acidic catalyst used to total aniline used in the end state: n(7)/n(1)(E).

Transition state T between starting state and end state (corresponding to the period of the change in load):

mass flow rate $m_1$ of total aniline used in the transition state: $m_1(T) \neq 0$ [e.g. in t/h], mass flow rate $m_2$ of total formaldehyde used in the transition state: $m_2(T) \neq 0$ [e.g. in t/h], mass flow rate $m_7$ of total acidic catalyst used in the end state: $m_7(E) \neq 0$ [e.g. in t/h], molar ratio n(1)/n(2) of total aniline used (1) to total formaldehyde used (2) in the transition state: n(1)/n(2)(T), molar ratio n(7)/n(1) of total acidic catalyst used (7) to total aniline used in the transition state: n(7)/n(1)(T).

According to the invention, the transition state begins as soon as $m_2$ is increased or lowered proceeding from $m_2(A)$ (this time is referred to hereinafter as $t_1$), and it ends as soon as $m_2$ reaches the target value for $m_2(E)$ (this time is referred to hereinafter as $t_2$).

On the basis of the minimum value for n(1)/n(2) of 1.6 used in the process of the invention, the yield of MDA target product is limited by the flow rate of total formaldehyde used (2) which is introduced. The maximum possible flow rate of total formaldehyde used (2) for preparation of a particular product type (i.e. a mixture of di- and polyamines of the diphenylmethane series characterized by a particular isomer composition of MMDA and a particular ratio of MMDA to PMDA) under the given boundary conditions of the production plant (10 000):

$m_2(N)$ [e.g. in t/h], is referred to here and hereinafter as nameplate load.

The maximum possible flow rate of total formaldehyde used (2) may vary according to the MDA product type to be prepared. This is generally unimportant for the present invention since the product after the change in load is essentially the same as before the change in load. If the changes in $n(1)/n(2)$ that are permissible in accordance with the invention, contrary to expectation, should lead to significant deviation in the nameplate load in the end state from that in the starting state, it is the nameplate load in the starting state $m_2(N, A)$ that is crucial for the purposes of the present invention (i.e. more particularly for the purpose of quantification of the change in load; for details see below). The value of $m_2(N, A)$ for a given production plant is either known from the outset (for example because the plant was designed for the production of a particular amount of a particular product type per hour) or can be easily determined by the person skilled in the art from the known boundary conditions of the plant (number and size of apparatuses present and the like) for the known operating parameters of the crucial starting state $(n(1)/n(2)(A), n(7)/n(1)(A))$. In practice, rather than $m_2(N)$, the corresponding product flow rate of MDA (e.g. in t/h) which is to be expected under the assumption of the design parameters for the production plant (including $n(1)/n(2)$ ratio, $n(7)/n(1)$ ratio etc.) is frequently reported. Rather than nameplate load, reference is therefore also frequently made to nameplate production capacity or else nameplate capacity for short. In this connection, the terms "load" and "(production) capacity" ultimately mean the same thing, but have different reference points (flow rate of starting material in one case and flow rate of target product to be expected from this starting material in the other case).

The actual load (or—see the above elucidations—the actual production capacity or capacity for short) in the starting state and end state, defined by the actual mass flow rate of total formaldehyde used in the starting state or end state, can then be expressed in relation to the nameplate load as follows:

$m_2(A) = X(A) \cdot m_2(N)$ [e.g. in t/h];
$m_2(E) = X(E) \cdot m_2(N)$ [e.g. in t/h].

In both cases, X is a dimensionless multiplier greater than 0 and less than or equal to 1 that expresses the actual load in relation to the nameplate load. In the event of a change from production at half the nameplate load ("half-load") to production with nameplate load ("full load"), accordingly, $X(A) = \frac{1}{2}$ and $X(E) = 1$. In the case of increases in load, $X(E) > X(A)$; in the case of reductions in load, $X(E) < X(A)$.

A quantitative measure for the size of a change in load is the magnitude of the differential of $X(E)$ and $X(A)$:

$$|X(E) - X(A)| (= |X(A) - X(E)|) = \Delta X$$

In the context of this invention, a change in load is one with a value of $\Delta X$ of not less than 0.10, preferably of not less than 0.15, more preferably of not less than 0.20, most preferably of not less than 0.25. The process of the invention comprises at least one change in load as thus defined.

In all abovementioned states of operation, $n(1)/n(2)$ is set to a value of greater than 1.6. With regard to the expression "total acidic catalyst used", the statements made above for aniline and formaldehyde are correspondingly applicable: what is meant is the total amount of acidic catalyst. This can be (and preferably) fed entirely to the reactor 3000-1; alternatively, it is possible to supply this reactor with just the majority of the total acidic catalyst used and to meter smaller proportions additionally into the reactors that follow in flow direction.

In any case, the aim is to avoid unwanted changes in the product composition resulting from the change in load. Since changes in the product composition are determined crucially by changes in the $n(1)/n(2)$ ratio, the process of the invention is operated in such a way that:

$$0.95 \cdot n(1)/n(2)(A) \leq n(1)/n(2)(E) \leq 1.05 \cdot n(1)/n(2)(A),$$
preferably $$0.97 \cdot n(1)/n(2)(A) \leq n(1)/n(2)(E) \leq 1.03 \cdot n(1)/n(2)(A).$$

According to the invention, the temperature in each of the reactors downstream in flow direction (3000-2, 3000-3, . . . 3000-i) is set to a value more than 2.0° C. above $T_{3000-1}$. This is also true in all states of operation, i.e. in the starting state, transition state and end state.

According to the invention, moreover, the temperature in the first reactor in flow direction (3000-1) is always chosen such that it is within the range from 25.0° C. to 65.0° C., preferably 30.0° C. to 60.0° C. This is true in all states of operation, i.e. in the starting state, transition state and end state.

With regard to the amounts of aniline and acidic catalyst used, the process according to the invention is operated in such a way that:

$$0.90 \cdot n(7)/n(1)(A) \leq n(7)/n(1)(E) \leq 1.10 \cdot n(7)/n(1)(A),$$
preferably $$0.95 \cdot n(7)/n(1)(A) \leq n(7)/n(1)(E) \leq 1.05 \cdot n(7)/n(1)(A).$$

Moreover, during the transition state T:

(i) $n(1)/n(2)(T)$ is adjusted such that the following is always true throughout the transition state:

$$0.90 \cdot n(1)/n(2)(A) \leq n(1)/n(2)(T) \leq 1.10 \cdot n(1)/n(2)(A),$$
preferably $$0.95 \cdot n(1)/n(2)(A) \leq n(1)/n(2)(T) \leq 1.05 \cdot n(1)/n(2)(A);$$

(ii) $n(7)/n(1)(T)$ is adjusted such that the following is always true throughout the transition state:

$$0.85 \cdot n(7)/n(1)(A) \leq n(7)/n(1)(T) \leq 1.15 \cdot n(7)/n(1)(A),$$
preferably $$0.90 \cdot n(7)/n(1)(A) \leq n(7)/n(1)(T) \leq 1.10 \cdot n(7)/n(1)(A);$$

(iii) the temperature in the first reactor in flow direction (3000-1) from step (A-II) is set to a value that differs from the temperature in this reactor during the starting state A by a maximum of 10.0° C., preferably by a maximum of 5.0° C., more preferably by a maximum of 2.0° C., the particularly preferred maximum deviation by ±2.0° C. being regarded as the same temperature for all practical purposes, and (iv-1) in the case that $m_2(E) > m_2(A)$, the temperature in at least one (preferably in all) of the reactors downstream in flow direction (3000-2, . . . , 3000-i), by comparison with the starting state A, is increased by more than 2.0° C., and so the target end temperature is reached at least at the time at which $m_2$ has reached the target value for $m_2(E)$ (i.e. at $t = t_2$), and in all reactors (3000-2, . . . , 3000-i) in which the temperature is not increased it is kept the same within the range of ±2.0° C.;

(iv-2) in the case that $m_2(E) < m_2(A)$, the temperature in at least one (preferably in all) of the reactors downstream in flow direction (3000-2, . . . , 3000-i), by comparison with the starting state A, is lowered by more than 2.0° C., and so the target end temperature is reached at least at the time at which $m_2$ has reached the target value for $m_2(E)$ (i.e. at $t=t_2$), and in all reactors (3000-2, ..., 3000-$i$) in which the temperature is not lowered it is kept the same within the range of $\pm 2.0°$ C.;

According to the invention, for the reactor 3000-1 during the transition state, a significant deviation from the temperature in the starting state is possible. In this reactor, changes in the amount of heat released as a consequence of the change in load are manifested to an enhanced degree. (Significant contributions to exothermicity are firstly the heat of neutralization which is released in the reaction of the acid with the aminic components of the reaction mixture, and the acid-catalyzed rearrangement of the aminal that sets in.) This can be taken into account if required by greater tolerances in the temperature in the transition state. However, it is preferable, at the end of the transition state (i.e. when $m_2$ has reached the target value for $m_2(E)$), to adjust the temperature in the reactor 3000-1 back to a value which corresponds to that of the starting state within a range of variation of $\pm 2.0°$ C. and to then maintain this temperature in the end state. It is further preferable to maintain the temperature that exists in the reactors 3000-2, ..., 3000-$i$ at the end of the transition state (i.e. at $t_2$) within a range of variation of $\pm 2.0°$ C. in the end state.

The increase in temperature in at least one of the reactors 3000-2, ..., 3000-$i$ in the case of an increase in load should be undertaken very rapidly in order to be able to compensate for the shortening of the residence time in the best possible way. Preferably, the target temperature for the end state is already established as the new target temperature at $t_1$, such that the actual existing temperature assumes the target value for the end state within the shortest possible time, but no later than at $t_2$.

The decrease in temperature in at least one of the reactors 3000-2, ..., 3000-$i$ in the case of a decrease in load, by contrast, should be undertaken very slowly in order to avoid the formation of unrearranged products. Preferably, the target temperature for the end state is not attained until $t_2$.

Figure 1:
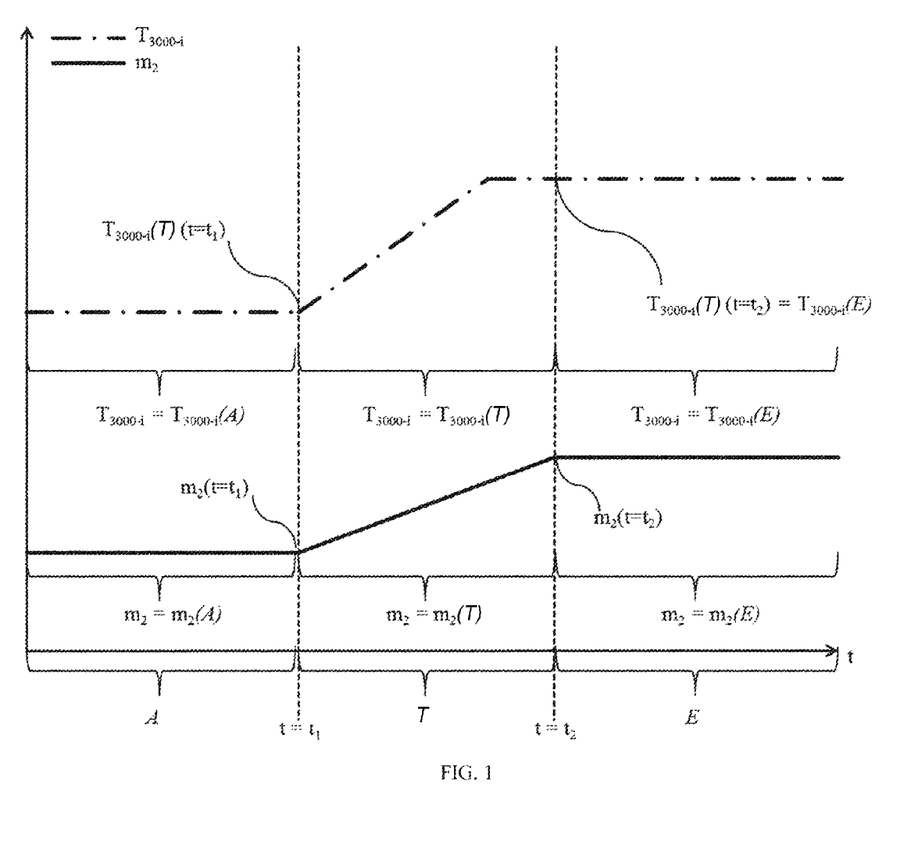
FIG. 1 illustrates the procedure of the invention showing the temperature $T_{3000-i}$ in the last reactor of the reactor cascade and the flow rate $m_2$, each as a function of time t.

The appended drawings are intended to illustrate the procedure of the invention:

FIG. 1 shows the temperature $T_{3000-i}$ in the last reactor of the reactor cascade and the flow rate $m_2$, each as a function of time t.

This and the other drawings are merely intended to illustrate the basic principle of the invention and do not make any claim to be true to scale.

It is essential to the invention that, at the end of the transition state (i.e. when the target load for the end state has been established, at $t=t_2$), in the event of an increase in load, the temperature in at least one of the reactors 3000-2, ..., 3000-$i$ has been increased by more than $2.0°$ C. In the case of a decrease in load, the procedure is the reverse (lowering of the temperature in at least one of the reactors 3000-2, ..., 3000-$i$ by more than $2.0°$ C.). The procedure of the invention is illustrated in FIG. 1 using the example of an increase in load and the temperature $T_{3000-i}$ in the last reactor of the reactor cascade: in the starting state, the load $m_2=m_2(A)$. At time $t=t_1$ (=commencement of the transition state), the load is increased until, at time $t=t_2$ (=end of the transition state), it has reached the target value for the end state $m_2=m_2(E)$. The temperature $T_{3000-i}$ is likewise increased until it reaches, at (no later than) $t=t_2$, the target value increased by more than $2.0°$ C. compared to $T_{3000-i}$(A). In the illustrative case shown in FIG. 1, this temperature is already attained before $t_2$, which is preferable in the event of increases in load, as elucidated above. For all conceivable configurations of the invention and not just in the cases exemplified in FIG. 1, $m_2(t=t_2)=m_2(E)$ and $T_{3000-i}(T)(t=t_2)=T_{3000-i}(T)(E)$.

Embodiments of the invention are described in detail hereinafter. These embodiments, unless stated otherwise in the specific case, are applicable to all process regimes of the invention. It is possible here to combine various embodiments with one another as desired, unless the opposite is apparent to the person skilled in the art from the context.

Figure 2:
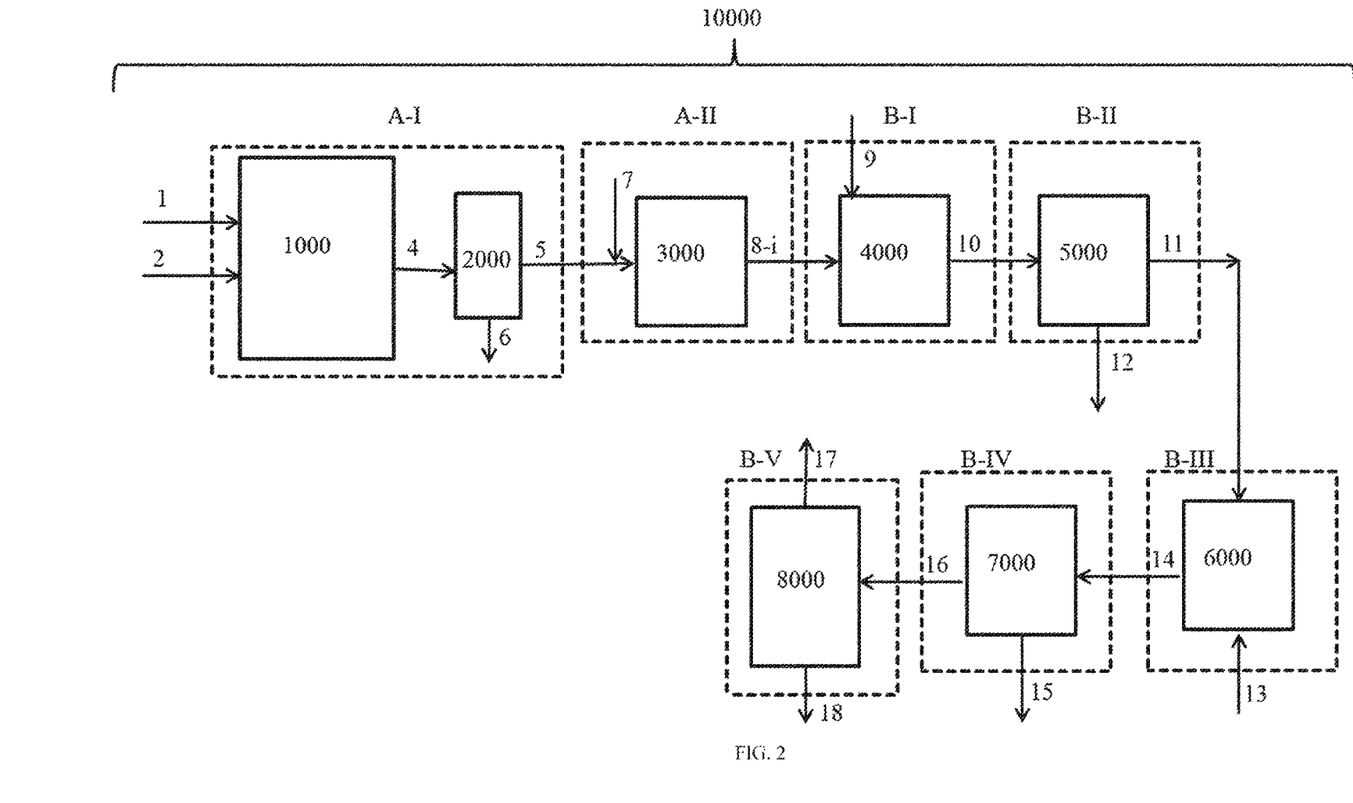
FIG. 2 illustrates a production plant suitable for the performance of the process of the invention.

FIG. 2 shows a production plant (10 000) suitable for the performance of the process of the invention.

Figure 3:
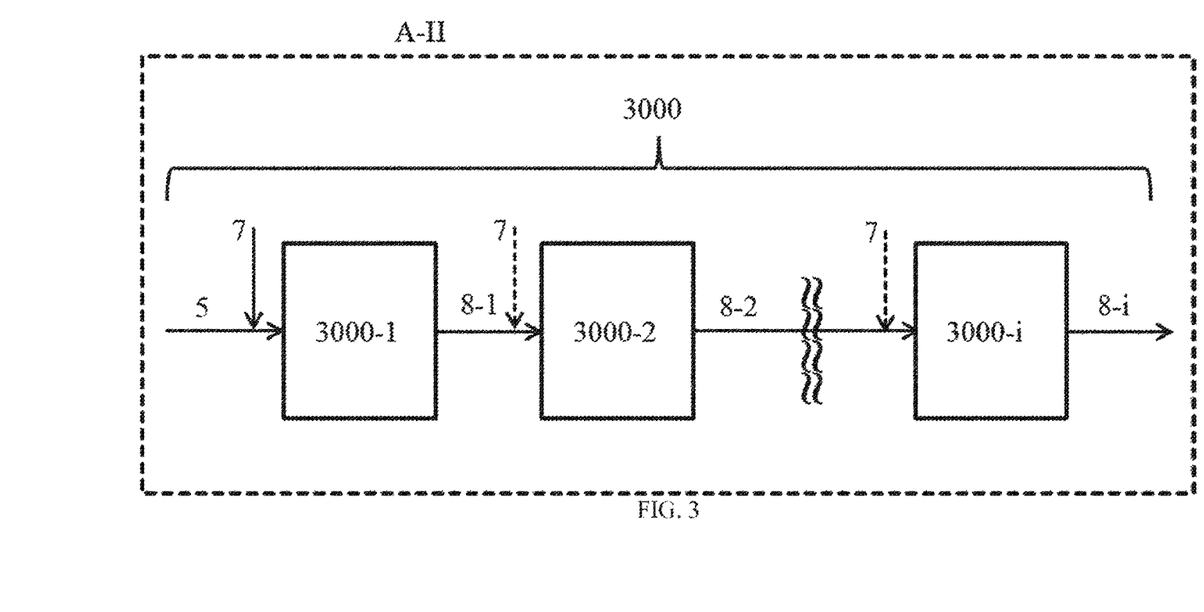
FIG. 3 shows a detail of the reactor cascade.

FIG. 3 shows a detail of the reactor cascade (3000). The merely optional addition of further acidic catalyst (7) to the reactors (3000-2) to (3000-$i$) downstream of the reactor (3000-1) is shown by dotted arrows.

Step (A-I) of the process of the invention, provided that the other requirements of the invention are complied with, can be conducted as known in principle from the prior art. Aniline and aqueous formaldehyde solution are preferably condensed here at molar ratios in the range from 1.6 to 20, preferably 1.6 to 10 and more preferably 1.6 to 6.0, even more preferably of 1.7 to 5.5 and very exceptionally preferably of 1.8 to 5.0, at temperatures of $20.0°$ C. to $120.0°$ C., preferably $40.0°$ C. to $110.0°$ C. and more preferably $60.0°$ C. to $100.0°$ C., to give aminal and water. The reactor of step (A-I) is operated at standard pressure or under elevated pressure. There is preferably a pressure of 1.05 bar to 5.00 bar (absolute), very preferably of 1.10 bar to 3.00 bar (absolute) and most preferably of 1.20 bar to 2.00 bar (absolute). The pressure is maintained by pressure-regulating valves, or by connecting the off-gas systems of aminal reactor (1000) and the overflow from the aminal separator (2000) used for phase separation on completion of reaction. The aminal separator and the outlet for the aqueous phase are preferably heated in order to prevent caking.

Suitable aniline qualities are described, for example, in EP 1 257 522 B1, EP 2 103 595 A1 and EP 1 813 598 B1. Preference is given to using technical grade qualities of formalin (aqueous solution of formaldehyde) with 30.0% by mass to 50.0% by mass of formaldehyde in water. However, formaldehyde solutions with lower or higher concentrations or else the use of gaseous formaldehyde are also conceivable.

The phase separation of organic aminal phase and aqueous phase is preferably effected at temperatures of $20.0°$ C. to $120.0°$ C., more preferably of $40.0°$ C. to $110.0°$ C. and most preferably of $60.0°$ C. to $100.0°$ C., in each case preferably at ambient pressure or at slightly elevated pressure relative to ambient pressure (elevated by up to 0.10 bar).

Step (A-II) of the process of the invention, provided that the other requirements of the invention are complied with, can be conducted as known in principle from the prior art. The aminal is rearranged in the presence of an acidic catalyst, typically a strong mineral acid such as hydrochloric acid. Preference is given to the use of mineral acid in a molar ratio of mineral acid to aniline of 0.0010 to 0.90, preferably 0.050 to 0.50. It is of course also possible to use solid acidic catalysts as described in the literature. Formaldehyde can be added here to a mixture of aniline and acidic catalyst, and the reaction solution can be fully reacted by stepwise heating. Alternatively, aniline and formaldehyde can first be pre-reacted and then, with or without prior removal of water, admixed with the acidic catalyst or a mixture of further aniline and acidic catalyst, and then the reaction solution is fully reacted by stepwise heating. This reaction can be executed continuously or batch-wise by one of the numerous methods described in the literature (for example in EP 1 616 890 A1 or EP 127 0544 A1).

It is possible to supply the first reactor 3000-1 with further aniline and/or further formaldehyde. It is likewise possible to supply the downstream reactors 3000-2, ..., 3000-i with small amounts of aniline and/or formaldehyde. These may each be fresh feedstocks or recycle streams from other reactors. However, the majority of total aniline used and of total formaldehyde used is introduced into the "aminal reactor" 1000. Regardless of how aniline (1) and formaldehyde (2) are distributed, optionally over various reactors, the process of the invention is preferably conducted in such a way that the molar ratio of total aniline used (1) to total formaldehyde used (2), n(1)/n(2), in all states of operation (A, T, E) always has a value of 1.6 to 2.0, preferably of 1.6 to 10 and more preferably of 1.6 to 6.0, even more preferably of 1.7 to 5.5 and very exceptionally preferably of 1.8 to 5.0. Preferably, all the acidic catalyst used (7) is fed completely to reactor 3000-1. Alternatively, it is possible to feed a portion of the total acidic catalyst used (7) to one or more of the downstream reactors 3000-2, ..., 3000-i in flow direction.

The acidic catalyst (7) used in the process of the invention is preferably a mineral acid, especially hydrochloric acid. Suitable hydrochloric acid qualities are described, for example, in EP 1 652 835 A1.

Suitable reactors 3000-1, 3000-2, ... 3000-i in step (A) in both process regimes are apparatuses known to those skilled in the art, such as stirred tanks and tubular reactors:

In the case of stirred tank reactors, the temperature is generally the same throughout the reactor contents, and so, for the purposes of the present invention, it does not matter where the temperature is measured. If, contrary to expectation, significant temperature differences exist through the reactor contents, the temperature measured at the exit of the reaction mixture from the reactor is the crucial temperature for the purposes of the present invention.

If there is a significant temperature gradient between entry of the reaction mixture into the reactor and exit of the reaction mixture from the reactor, as may be the case in tubular reactors, the temperature measured at the exit of the reaction mixture from the reactor is the crucial temperature for the purposes of the present invention.

Preferably, the temperature in the reactors of the reactor cascade 3000 increases from reactor 3000-1 to reactor 3000-i, i.e. the temperature in the last reactor 3000-i is preferably higher than in the first reactor 3000-1, and the temperature in two successive reactors between 3000-1 and 3000-i may also be the same, but the temperature of each reactor 3000-2, 3000-3, ..., 3000-i is not lower than that of the preceding reactor. Preferably, however, the temperature in the reactors of the reactor cascade 3000 increases successively from reactor 3000-1 to reactor 3000-i, i.e. the temperature of each reactor 3000-2, 3000-3, ..., 3000-i is higher than that of the preceding reactor.

It is likewise preferable to set $T_{3000-1}$ always to a value of 25.0° C. to 65.0° C., more preferably 30.0° C. to 60.0° C., and the temperature in each of the reactors downstream in flow direction (3000-2, ..., 3000-i) always to a value of 35.0° C. to 200.0° C., more preferably of 50.0° C. to 180.0° C.

All the aforementioned figures for preferred temperatures are applicable in all states of operation (A, T, E).

The respective temperature $T_{3000-j}$ in a reactor j of the reactor cascade 3000 at the end of the transition state (i.e. when $m_2$ has reached the target value for the end state $m_2(E)$) is preferably retained within a range of variation of ±2.0° C. for the duration of production with the formaldehyde mass flow rate $m_2(E)$. At the temperature $T_{3000-j}$, in the terminology of the present invention, as already mentioned, slight variations within the range of ±2.0° C. are still considered to be the same temperature.

Step (B-I), provided that the other requirements of the invention are complied with, can be conducted as known in principle from the prior art. The reaction mixture comprising the di- and polyamines of the diphenylmethane series is optionally neutralized with addition of water and/or aniline. According to the prior art, the neutralization is typically effected at temperatures of, for example, 90.0° C. to 120.0° C. without addition of further substances. It can alternatively be effected at a different temperature level in order, for example, to accelerate the degradation of troublesome by-products. Suitable bases are, for example, the hydroxides of the alkali metal and alkaline earth metal elements. Preference is given to employing aqueous NaOH. The base used for neutralization is preferably used in amounts of greater than 100%, more preferably 105% to 120%, of the amount stoichiometrically required for the neutralization of the acidic catalyst used (see EP 1 652 835 A1).

Step (B-II), provided that the other requirements of the invention are complied with, can be conducted as known in principle from the prior art. The neutralized reaction mixture comprising the di- and polyamines of the diphenylmethane series is separated into an organic phase comprising di- and polyamines of the diphenylmethane series and an aqueous phase. This can be assisted by the addition of aniline and/or water. If the phase separation is assisted by addition of aniline and/or water, they are preferably added already with vigorous mixing in the neutralization. The mixing can be effected here in mixing zones with static mixers, in stirred tanks or stirred tank cascades, or else in a combination of mixing zones and stirred tanks. The neutralized reaction mixture diluted by addition of aniline and/or water is then preferably supplied to an apparatus which, owing to its configuration and/or internals, is particularly suitable for separation into an organic phase comprising MDA and an aqueous phase, preferably phase separation or extraction apparatuses according to the prior art, as described, for example, in Mass-Transfer Operations, 3rd Edition, 1980, McGraw-Hill Book Co, p. 477 to 541, or Ullmann's Encyclopedia of Industrial Chemistry (Vol. 21, Liquid-Liquid Extraction, E. Müller et al., pages 272-274, 2012 Wiley-VCH Verlag GmbH & Co. KGaA, Weinheim, DOI: 10.1002/14356007.b03_06.pub2) or in Kirk-Othmer Encyclopedia of Chemical Technology (see "http://onlinelibrary.wiley.com/book/10.1002/0471238961", Published Online: 15 Jun. 2007, pages 22-23) (mixer-settler cascades or settling vessels).

If, in step (A-II), during the transition state, the flow rate of acidic catalyst is increased significantly, the flow rate of base used in step (B-I) will of course also be increased correspondingly (and within the same timeframe), in order that the requirement of the invention for the stoichiometric excess of base is always fulfilled, i.e. even in the transition state. If, in step (A-II), during the transition state, the flow rate of acidic catalyst is lowered significantly, the flow rate of base used in step (B-I) will preferably also be lowered correspondingly (and likewise within the same timeframe), in order to avoid unnecessary salt burdens.

Step (B-II) is preferably followed by further workup steps, namely:

Step (B-III): washing the organic phase (11) in a washing unit (6000, "washing vessel") with washing liquid (13), followed by Step (B-IV): separating the mixture (14) obtained in step (B-III) in a separation unit (7000, "washing water separator") into an organic phase (16) comprising di- and polyamines of the diphenylmethane series and an aqueous phase (15);

Step (B-V): distilling the organic phase (16) from step (B-IV) in a distillation apparatus (8000) to obtain the di- and polyamines of the diphenylmethane series (18), with removal of a stream (17) comprising water and aniline.

These steps can be conducted as known in principle from the prior art. It is particularly preferable that there is a subsequent washing (B-III) of the organic phase (11) with water (13) and a new separation of the water phase (15) for removal of residual salt contents (preferably as described in DE-A-2549890, page 3). After exiting from the phase separation in step (B-IV), the organic phase (16) comprising di- and polyamines of the diphenylmethane series typically has a temperature of 80.0° C. to 150.0° C.

Water and aniline are separated by distillation from the organic phase thus obtained, comprising di- and polyamines of the diphenylmethane series, as described in EP 1 813 597 B1. The organic phase preferably has a composition, based on the mass of the mixture, of 5.0% to 15% by mass of water and, according to the use ratios of aniline and formaldehyde, 5.0% to 90% by mass, preferably 5.0% to 40% by mass, of aniline and 5.0% to 90% by mass, preferably 50% to 90% by mass, of di- and polyamines of the diphenylmethane series.

More preferably, the process of the invention also includes a further step (C) in which recycling of stream (17) comprising water and aniline, optionally after workup, into step (A-I) and/or, if the optional addition of further aniline (1) in step (A-II) is conducted, into step (A-II) is undertaken.

In all embodiments of the invention, the setting of the temperature in the reactors 3000-2, . . . , 3000-$i$ of the reactor cascade 3000 to the target values for the end state is concluded with the end of the change in load (i.e. as soon as the mass flow rate of total formaldehyde used $m_2$ has reached the target value for the end state $m_2(E)$; time $t_2$). The setting to the target temperature value for the end state is effected stepwise or continuously, preferably continuously. In the case of stepwise setting of the respective parameter, the setting preferably comprises multiple stages, meaning that the target end temperature is set via one or more intermediate values (each of which is retained for a particular period of time) between the starting temperature and the target end temperature.

If the other operating parameters (i.e. n(1)/n(2), n(7)/n(1), $T_{3000-1}$), within the limits permissible in accordance with the invention, are to be altered beyond the transition state (i.e. a change in the respective operating parameter to a new value in the end state), it is preferable that the required setting to the target values for the end state has likewise been concluded at time $t_2$. More particularly, the present invention therefore also relates to an embodiment in which the process, during the transition state T is operated such that the target values of n(1)/n(2), n(7)/n(1) for the end state E and the temperature in the first reactor 3000-1 of the reactor cascade 3000 exist as soon as the mass flow rate of total formaldehyde used $m_2$ has reached the target value $m_2(E)$ for the end state. The setting of the target values for the end state can again be effected stepwise or continuously, preferably continuously. In the case of stepwise setting of the respective parameter, the setting preferably comprises multiple stages, meaning that, for example, a target end temperature is established via one or more intermediate values (each of which is maintained for a particular period of time) between the starting temperature and the target end temperature.

In all embodiments of the invention, it is further preferable to restrict the change in load to a time not exceeding 120 minutes, i.e. to limit the period within which the mass flow rate of total formaldehyde used $m_2$ is adjusted proceeding from $m_2(A)$ to the target value for the end state $m_2(E)$ (=duration of the transition state=period of time from $t_i$ to $t_2$) is preferably to 120 minutes. The minimum duration of the transition state is preferably 1.00 minute, more preferably 5.00 minutes and most preferably 30.00 minutes.

Detailed configurations of the invention are elucidated in detail in the appended examples.

The di- and polyamines of the diphenylmethane series that are obtained in accordance with the invention can be reacted by the known methods, under inert conditions, with phosgene in an organic solvent to give the corresponding di- and polyisocyanates of the diphenylmethane series, the MDI. The phosgenation can be conducted here by any of the methods known from the prior art (e.g. DE-A-844896 or DE-A-19817691).

The procedure of the invention gives rise to the following advantages for the preparation of MDA:
 i) The productivity of the MDA plant is higher because the occurrence of off-spec material is minimized
 ii) The formation of unwanted by-products is likewise minimized.

Thus, the procedure of the invention, during a non-steady state (during the transition state), enables a technically seamless change in load without subsequent outage periods in the steady state (the end state) that follows with constantly high quality of the desired MDA end product. The process of the invention also enables a rapid change in load and hence rapid reaction to events such as raw material shortage, etc.

EXAMPLES

The results outlined in the examples for the bicyclic content, the isomer composition and the content of N-methyl-4,4'-MDA are based on calculations. The calculations are based partly on theoretical models and partly on process data collected in real operational experiments, the statistical evaluation of which created a mathematical correlation of running parameters and result (e.g. bicyclic content). The content of N-formyl-4,4'-MDA is reported on the basis of operational experience values. All percentages and ppm values reported are proportions by mass based on the total mass of the respective stream of matter. The proportions by mass in the real operational experiments that gave the basis for the theoretical model were ascertained by HPLC.

Reactor temperatures are based on the temperature of the respective process product at the exit from the reactor.

The MDA prepared, in all examples, has a residual aniline content in the range from 50 ppm to 100 ppm and a water content in the range from 200 ppm to 300 ppm.

A. Reduction in Load Proceeding from Production with Nameplate Load

I. General Conditions for the Preparation of MDA in a Run-in Production Plant at Nameplate Load In a continuous reaction process, 23.20 t/h of feed aniline (containing 90.0% by mass of aniline, 1) and 9.60 t/h of 32% aqueous formaldehyde solution (corresponding to a molar ratio of aniline (1): formaldehyde (2) of 2.25:1) are mixed and converted to the aminal (3) at a temperature of 90.0° C.

and a pressure of 1.40 bar (absolute) in a stirred reaction tank (1000). The reaction tank is provided with a cooler having a cooling circuit pump. The reaction mixture leaving the reaction tank is fed into a phase separation apparatus (aminal separator, 2000) (step (A-I)).

After the phase separation to remove the aqueous phase (6), the organic phase (5) is admixed in a mixing nozzle with 30% aqueous hydrochloric acid (7) (protonation level 10%, i.e. 0.10 mol of HCl is added per mole of amino groups) and run into the first rearrangement reactor (3000-1). The first rearrangement reactor (called "vacuum tank") is operated at 50.0° C., which is ensured by means of evaporative cooling in a reflux condenser at a pressure of 104 mbar (absolute). The reflux condenser is charged with 0.50 t/h of fresh aniline. The rearrangement reaction is conducted to completion in a reactor cascade composed of a total of seven reactors at 50.0° C. to 156.0° C. (i.e. 50.0° C. in reactor 3000-1/60.0° C. in reactor 3000-2/83.0° C. in reactor 3000-3/104.0° C. in reactor 3000-4/119.0° C. in reactor 3000-5/148.0° C. in reactor 3000-6/156.0° C. in reactor 3000-7) (step (A-II)).

On completion of reaction, the reaction mixture (8-i) obtained is admixed with 32% sodium hydroxide solution in a molar ratio of 1.10:1 sodium hydroxide to HCl and reacted in a stirred neutralization vessel (4000) (step (B-I)). The temperature here is 115.0° C. The absolute pressure is 1.40 bar. The neutralized reaction mixture (10) is then separated in a neutralization separator (5000) into an aqueous lower phase (12), which is fed to a wastewater collection vessel, and into an organic phase (11) (step (B-II)).

The organic upper phase (11) is fed to the washing and washed with condensate (13) in a stirred washing vessel (6000) (step (B-III)). After the washing water (15) has been separated from the biphasic mixture (14) obtained in the washing vessel (6000) in a washing water separator (7000, step (B-IV)), the crude MDA (16) thus obtained is freed of water and aniline (removed together as stream 17) by distillation, and 17 t/h of MDA (18) were obtained as bottom product (step (B-V)).

MDA prepared in this way has an average composition of 45.2% 4,4'-MDA, 5.5% 2,4'-MDA, 0.3% 2,2'-MDA, i.e. a total bicyclic content of 51.0% and also 0.3% N-methyl-4,4'-MDA and 0.3% N-formyl-4,4'-MDA, the remainder to 100% consisting essentially of higher homologs (PMDA) and isomers thereof.

Example 1 (Comparative Example): Reduction in Load of the MDA Plant from Nameplate Load to Half-Load (=50% of Nameplate Load), where the n(1)/n(2) Ratio is Kept the Same, the Aniline, Formalin and Sodium Hydroxide Solution Feedstocks are Reduced Simultaneously and HCl is Reduced in a Time-Delayed Manner, the Temperature in the Vacuum Tank (3000-1) Remains the Same and is Lowered by More than 2.0° C. in the Last Five of the Reactors 3000

The MDA plant, as described above under A.I, is operated at a load of 17.0 t/h of MDA. Owing to lower product demand the production load is to be halved. For this purpose, at the same time, the feed rates of aniline and formalin to the aminal reactor (1000) are adjusted to the new production load within 120 minutes. The formalin rate is reduced to 4.80 t/h. The aniline feed rate is reduced to 11.35 t/h. The flow rate of hydrochloric acid into the mixing nozzle in the feed to the first rearrangement reactor (3000-1) is halved with a delay of 60 minutes which results in a temporary increase in the n(7)/n(1) ratio to 0.20 during the transition state. The first rearrangement reactor is still operated at 50.0° C., which is ensured by means of the evaporative cooling in the reflux condenser at 104 mbar (absolute). The reflux condenser is still charged with 0.50 t/h of fresh aniline. The rearrangement reaction is conducted to completion in a reactor cascade at 50.0° C. to 145.0° C. (50.0° C. in reactor 3000-1/60.0° C. in reactor 3000-2/80.0° C. in reactor 3000-3/96.0° C. in reactor 3000-4/116.0° C. in reactor 3000-5/142.0° C. in reactor 3000-6/145.0° C. in reactor 3000-7). On completion of reaction, the reaction mixture obtained, as described in the general conditions for preparation of MDA, is neutralized with sodium hydroxide solution, with reduction of the amount of sodium hydroxide solution within the same time window as formalin and aniline, and then worked up to give MDA (18). Neutralization vessel, separator, base washing, distillation receiver distillation and product vessel become acidic. Black steel as installed in the distillation, for example, is attacked. All apparatuses have to be completely emptied, rinsed with condensate, then rinsed with aniline, and the entire acidic product mixture, for workup, has to be run into the reactor cascade (i.e. into the fourth rearrangement reactor 3000-4) at a suitable point. The time taken for that runs to four days.

Example 2 (Inventive): Reduction in Load of the MDA Plant from Nameplate Load to Half-Load, where the n(1)/n(2) Ratio is Kept the Same, the Aniline and Formalin Feedstocks, HCl and Sodium Hydroxide Solution are Reduced Simultaneously, the Temperature in the Vacuum Tank (3000-1) Remains the Same and the Temperature is Lowered by More than 2.0° C. in the Last Five of the Reactors 3000

The MDA plant, as described above under A.I, is operated at a load of 17.0 t/h of MDA. Owing to lower product demand the production load is to be halved. For this purpose, at the same time, the feed rates of aniline and formalin to the aminal reactor (1000) are adjusted to the new production load within 120 minutes. The formalin rate is reduced to 4.80 t/h. The aniline feed rate is reduced to 10.85 t/h. The flow rate of hydrochloric acid into the mixing nozzle in the feed to the first rearrangement reactor is reduced within the same period as aniline and formalin with constant retention of the protonation level of 10% (i.e. with retention of the n(7)/n(1) ratio). The first rearrangement reactor (3000-1) is still operated at 50.0° C., which is ensured by means of the evaporative cooling in the reflux condenser at 104 mbar (absolute). The reflux condenser is still charged with 0.50 t/h of fresh aniline. The rearrangement reaction is conducted to completion in a reactor cascade at 50.0° C. to 147° C. (50.0° C. in reactor 3000-1/60.0° C. in reactor 3000-2/80.0° C. in reactor 3000-3/95.0° C. in reactor 3000-4/117.0° C. in reactor 3000-5/143.0° C. in reactor 3000-6/147.0° C. in reactor 3000-7) (step (A-II)). On completion of reaction, the reaction mixture obtained, as described in the general conditions for preparation of MDA, is neutralized with sodium hydroxide solution, with reduction of the amount of sodium hydroxide solution within the same time window as formalin and aniline and HCl with retention of the molar ratio of 1.10:1 sodium hydroxide solution to HCl, and then worked up to give the desired MDA type, obtaining 8.5 t/h of MDA (18) as the bottom product from the distillation.

40 hours after commencement of the change in load, the MDA in the feed to the MDA tank has a composition of 46.5% 4,4'-MDA, 5.0% 2,4'-MDA, 0.2% 2,2'-MDA, i.e. a total bicyclic content of 51.7% and also 0.3% N-methyl-4,4'-MDA and 0.3% N-formyl-4,4'-MDA, the remainder to 100% consisting essentially of higher homologs (PMDA) and isomers thereof. The product differs only insignificantly from the NMA stream (18) which is obtained on average in production at nameplate capacity as described in the general conditions for the preparation of MDA in a run-in production plant at nameplate load.

Table 1 below compares the results from section A.

TABLE 1

Comparison of the examples from section A

|  | Starting state Nameplate load | End state Half-load Example 1 (comp.) | End state Half-load Example 2 (inv.) |
|---|---|---|---|
| Aniline (90%) in reactor 1000 [t/h] | 23.20 | 11.35 | 11.35 |
| Aniline in reactor 3000-1 [t/h] | 0.50 | 0.50 | 0.50 |
| Formalin (32%) in reactor 1000 [t/h] | 9.60 | 4.80 | 4.80 |
| n(1)/n(2) | 2.25 | 2.25 | 2.25 |
| Protonation level [%] | 10 | 10 | 10 |
| n(7)/n(1) | 0.10 | 0.10 | 0.10 |
| Temp. gradient in reactor cascade 3000 [° C.] | 50.0 → 156.0 | 50.0 → 145.0 | 50.0 → 147.0 |
| T(3000-1) [° C.] | 50.0 | 50.0 | 50.0 |
| T(3000-2) [° C.] | 60.0 | 60.0 | 60.0 |
| T(3000-3) [° C.] | 83.0 | 80.0 | 80.0 |
| T(3000-4) [° C.] | 104.0 | 96.0 | 95.0 |
| T(3000-5) [° C.] | 119.0 | 116.0 | 117.0 |
| T(3000-6) [° C.] | 148.0 | 142.0 | 143.0 |
| T(3000-7) [° C.] | 156.0 | 145.0 | 147.0 |
| Production capacity [t/h] | 17.00 | 8.50 | 8.50 |
| 4,4'-MDA [%] | 45.2 | — | 46.5 |
| 2,4'-MDA [%] | 5.5 | — | 5.0 |
| 2,2'-MDA [%] | 0.3 | — | 0.2 |
| N-methyl-MDA [%] | 0.3 | — | 0.3 |
| N-formyl-MDA [%] | 0.3 | — | 0.3 |
| Bicyclic content [%] | 51.0 | — | 51.7 |
| Comment | — | Production had to be stopped | Product has comparable composition and a similar by-product spectrum to the product in the starting state |

B. Increase in Load Proceeding from Production at Half-Load

I. General Conditions for the Preparation of MDA in a Run-in Production Plant at Half-Load The reaction is operated as described above under A.I for nameplate load with the following differences:

11.35 t/h of feed aniline (containing 90.0% by mass of aniline);

4.80 t/h of 32% aqueous formaldehyde solution (i.e. the molar ratio of aniline:formaldehyde is 2.25:1);

50.0° C. in reactor 3000-1/60.0° C. in reactor 3000-2/81.0° C. in reactor 3000-3/95.0° C. in reactor 3000-4/116.0° C. in reactor 3000-5/144.0° C. in reactor 3000-6/146.0° C. in reactor 3000-7;

Bottom product of 8.50 t/h of MDA (18).

MDA prepared in this way has an average composition of 46.3% 4,4'-MDA, 5.0% 2,4'-MDA, 0.2% 2,2'-MDA, i.e. a total bicyclic content of 51.5% and also 0.3% N-methyl-4,4'-MDA and 0.3% N-formyl-4,4'-MDA, the remainder to 100% consisting essentially of higher homologs (PMDA) and isomers thereof.

II. Target End State: Production at Nameplate Load

Example 3 (Comparative Example): Increase in Load of the MDA Plant from Half-Load to Nameplate Load, where the n(1)/n(2) Ratio and the n(7)/n(1) Ratio are Kept the Same, the Aniline and Formalin, HCl and Sodium Hydroxide Solution Feedstocks are Increased Simultaneously and the Temperature in all the Reactors 3000 Remains the Same within the Range of ±2.0° C.

The MDA plant, as described above under B.I, is operated at a load of 8.50 t/h of MDA. Owing to higher product demand the production load is to be doubled to nameplate load. For this purpose, at the same time, the feed rates of aniline and formalin to the aminal reactor are adjusted to the new production load within 120 minutes. The formalin rate was increased to 9.60 t/h. The aniline feed rate was increased to 23.20 t/h. The flow rate of hydrochloric acid into the mixing nozzle in the feed to the first rearrangement reactor is increased within the same period as aniline and formalin with retention of the protonation level of 10% (i.e. with retention of the n(7)/n(1) ratio). The first rearrangement reactor (3000-1) is still operated at 50.0° C., which is ensured by means of the evaporative cooling in the reflux condenser at 104 mbar (absolute). The reflux condenser is charged with 0.50 t/h of fresh aniline. The rearrangement reaction is conducted to completion in the reactor cascade at 50.0° C. to 145° C. (50.0° C. in reactor 3000-1/60.0° C. in reactor 3000-2/82.0° C. in reactor 3000-3/96.0° C. in reactor 3000-4/117.0° C. in reactor 3000-5/142.0° C. in reactor 3000-6/145.0° C. in reactor 3000-7).

After the reaction, the reaction mixture obtained is admixed with 32% sodium hydroxide solution in a molar ratio of 1.10:1 sodium hydroxide solution to HCl and reacted in a stirred neutralization vessel, increasing the amount of sodium hydroxide solution within the same time window as formalin, aniline and HCl with retention of the molar ratios. The further workup is effected as described above in production under nameplate load conditions. At the end of the transition state, 17.0 t/h of a bottom product are obtained.

Result: "MDA" thus prepared has not been completely rearranged and still contains partly rearranged products such as aminobenzylanilines, which lead to quality problems in the subsequent phosgenation to give MDI, for example distinctly elevated color values in the resulting MDI product. The MDA thus prepared, and also the resulting MDI, are off-spec product.

Example 4 (Inventive): Increase in Load of the MDA Plant from Half-Load to Nameplate Load, where the n(1)/n(2) Ratio is Kept the Same, the Aniline and Formalin Feedstocks, HCl and Sodium Hydroxide Solution are Increased Simultaneously, and the Temperature is Increased by More than 2.0° C. in the Last Four of the Reactors 3000

The MDA plant, as described above under B.I, is operated at a load of 8.50 t/h of MDA. Owing to higher product demand the production load is to be doubled to nameplate load. For this purpose, at the same time, the feed rates of aniline and formalin to the aminal reactor are adjusted to the new production load within 120 minutes. The formalin rate is increased to 9.60 t/h. The aniline feed rate is increased to 23.20 t/h. The flow rate of hydrochloric acid into the mixing nozzle in the feed to the first rearrangement reactor is adjusted within the same period as aniline and formalin with retention of the protonation level of 10% (i.e. with retention of the n(7)/n(1) ratio). The first rearrangement reactor (3000-1) is still operated at 50.0° C., which is ensured by means of the evaporative cooling in the reflux condenser at 104 mbar (absolute). The reflux condenser is charged with 0.50 t/h of fresh aniline. The rearrangement reaction is conducted to completion in the reactor cascade at 50.0° C. to 156° C. (50.0° C. in reactor 3000-1/60.0° C. in reactor 3000-2/83.0° C. in reactor 3000-3/104.0° C. in reactor 3000-4/119.0° C. in reactor 3000-5/148.0° C. in reactor 3000-6/156.0° C. in reactor 3000-7) (step A-II)).

After the reaction, the reaction mixture obtained is admixed with 32% sodium hydroxide solution in a molar ratio of 1.10:1 sodium hydroxide solution to HCl and reacted in a stirred neutralization vessel. The temperature is 115.0° C. The absolute pressure is 1.40 bar. The further workup is effected as described above in production under nameplate conditions. At the end of the transition state, the bottom product obtained is 17.0 t/h of MDA (18).

20 hours after commencement of the change in load, the MDA in the feed to the MDA tank has a composition of 45.2% 4,4'-MDA, 5.5% 2,4'-MDA, 0.3% 2,2'-MDA, i.e. a total bicyclic content of 51.0% and also 0.3% N-methyl-4,4'-MDA and 0.3% N-formyl-4,4'-MDA, the remainder to 100% consisting essentially of higher homologs (PMDA) and isomers thereof. The product differs only insignificantly from the MDA stream (18) which is obtained in production at half load as described in the general conditions for the preparation of MDA in a run-in production plant at half load.

Table 2 below compares the results from section B.

TABLE 2

Comparison of the examples from section B

| | Starting state Half-load | End state Nameplate load Example 3 (comp.) | End state Nameplate load Example 4 (inv.) |
|---|---|---|---|
| Aniline (90%) in reactor 1000 [t/h] | 11.35 | 23.20 | 23.20 |
| Aniline in reactor 3000-1 [t/h] | 0.50 | 0.50 | 0.50 |
| Formalin (32%) in reactor 1000 [t/h] | 4.80 | 9.60 | 9.60 |
| n(1)/n(2) | 2.25 | 2.25 | 2.25 |
| Protonation level [%] | 10 | 10 | 10 |
| n(7)/n(1) | 0.10 | 0.10 | 0.10 |
| Temp. gradient in reactor cascade 3000° C. | 50.0 → 146.0 | 50.0 → 145.0 | 50.0 → 156.0 |
| T(3000-1) [° C.] | 50.0 | 50.0 | 50.0 |
| T(3000-2) [° C.] | 60.0 | 60.0 | 60.0 |
| T(3000-3) [° C.] | 81.0 | 82.0 | 83.0 |
| T(3000-4) [° C.] | 95.0 | 96.0 | 104.0 |
| T(3000-5) [° C.] | 116.0 | 117.0 | 119.0 |
| T(3000-6) [° C.] | 144.0 | 142.0 | 148.0 |
| T(3000-7) [° C.] | 146.0 | 145.0 | 156.0 |
| Production capacity [t/h] | 8.50 | 17.00 | 17.00 |
| 4,4'-MDA % | 46.3 | — | 45.2 |
| 2,4'-MDA % | 5.0 | — | 5.5 |
| 2,2'-MDA % | 0.2 | — | 0.3 |
| N-methyl-MDA % | 0.3 | — | 0.3 |
| N-formyl-MDA % | 0.3 | — | 0.3 |
| Bicyclic content % | 51.5 | — | 51.0 |
| Comment | — | MDA has not been completely rearranged and still contains partly rearranged products such as aminobenzylanilines which lead to quality problems in the subsequent phosgenation to give MDI, for example distinctly elevated color values | Product has comparable composition and a similar by-product spectrum to the product in the starting state |

The invention claimed is:

1. A process for preparing di- and polyamines of the diphenylmethane series from aniline (1) and formaldehyde (2) in a production plant (10 000), where the molar ratio of total aniline used (1) to total formaldehyde used (2), n(1)/n(2), is always greater than 1.6, comprising:
   (A-I) reacting aniline (1) and formaldehyde (2) in the absence of an acidic catalyst to obtain a reaction mixture (4) comprising an aminal (3), and then at least partly separating an aqueous phase (6) from the reaction mixture (4) to obtain an organic phase (5) comprising the aminal (3);
   (A-II) contacting the organic phase (5) which comprises the aminal and is obtained in step (A-I) with an acidic catalyst (7) in a reactor cascade (3000) composed of i reactors connected in series (3000-1, 3000-2, . . . , 3000-i), where i is a natural number from 2 to 10, wherein
   the first reactor (3000-1) in flow direction is operated at a temperature $T_{3000\text{-}1}$ in the range from 25.0° C. to 65.0° C. and is charged with stream (5) and acidic catalyst (7) and optionally with further aniline (1) and/or further formaldehyde (2),
   every reactor downstream in flow direction (3000-2, . . . , 3000-i) is operated at a temperature of more than 2.0° C. above $T_{3000\text{-}1}$ and is charged with the reaction mixture obtained in the reactor immediately upstream;
   (B) isolating the di- and polyamines of the diphenylmethane series from the reaction mixture (8-i) obtained from step (A-II) in the last reactor (3000-i) by a process comprising:
   (B-I) adding a stoichiometric excess of base (9), based on the total amount of acidic catalyst used (7), to the reaction mixture (8-i) obtained in the last reactor (3000-i) in step (A-II) to obtain a reaction mixture (10); and
   (B-II) separating the reaction mixture (10) obtained in step (B-I) into an organic phase (11) comprising di- and polyamines of the diphenylmethane series and an aqueous phase (12);
   wherein
   in the event of a change in the production capacity from a starting state A with
   a mass flow rate in the starting state of total aniline used of $m_1(A) \neq 0$,
   a mass flow rate in the starting state of total formaldehyde used of $m_2(A) = X(A) \cdot m_2(N)$, where $X(A)$ is a dimensionless number $>0$ and $\leq 1$ and $m_2(N)$ denotes the nameplate load of the production plant (10 000),
   a molar ratio in the starting state of total aniline used (1) to total formaldehyde used (2) of n(1)/n(2)(A), a molar ratio in the starting state of total acidic catalyst used to total aniline used of n(7)/n(1)(A)

to an end state E with
a mass flow rate in the end state of total aniline used of $m_1(E) \neq 0$,
a mass flow rate in the end state of total formaldehyde used of $m_2(E) = X(E) \cdot m_2(N)$, where $X(E)$ is a dimensionless number >0 and ≤1,
a molar ratio in the end state of total aniline used (1) to total formaldehyde used (2) of n(1)/n(2)(E) and
a molar ratio in the end state of total acidic catalyst used to total aniline used of n(7)/n(1)(E);

by a quantity $\Delta X = |X(E) \cdot X(A)|$, with $\Delta X \geq 0.10$, wherein the process comprises at least one change in production capacity that commences at a time $t_1$ and concludes at a time $t_2$, wherein:

$$0.95 \cdot n(1)/n(2)(A) \leq n(1)/n(2)(E) \leq 1.05 \cdot n(1)/n(2)(A),$$

and $$0.90 \cdot n(7)/n(1)(A) \leq n(7)/n(1)(E) \leq 1.10 \cdot n(7)/n(1)(A),$$

characterized in that, in the period from $t_1$ to $t_2$, the transition state T, with a molar ratio of total aniline used (1) to total formaldehyde used (2) of n(1)/n(2)(T) and a molar ratio of total acidic catalyst used to total aniline used of n(7)/n(1)(T), (i) n(1)/n(2)(T) is adjusted such that the following is always true throughout the transition state:

$$0.90 \cdot n(1)/n(2)(A) \leq n(1)/n(2)(T) \leq 1.10 \cdot n(1)/n(2)(A);$$

(ii) n(7)/n(1)(T) is adjusted such that the following is always true throughout the transition state:

$$0.85 \cdot n(7)/n(1)(A) \leq n(7)/n(1)(T) \leq 1.15 \cdot n(7)/n(1)(A);$$

(iii) the temperature in the first reactor (3000-1) in flow direction from step (A-II) is adjusted to a value that differs from the temperature in that reactor during the starting state A by not more than 10.0° C., and (iv-1) in the case that $m_2(E) > m_2(A)$, the temperature in at least one of the reactors downstream in flow direction (3000-2, ..., 3000-*i*), by comparison with the starting state A, is increased by more than 2.0° C. in such a way that the target end temperature is reached no later than at time $t_2$, and in all reactors (3000-2, ..., 3000-*i*) in which the temperature is not increased it is kept the same within a range of variation of ±2.0° C.;

(iv-2) in the case that $m_2(E) < m_2(A)$, the temperature in at least one of the reactors downstream in flow direction (3000-2, ..., 3000-*i*), by comparison with the starting state A, is lowered by more than 2.0° C. in such a way that the target end temperature is reached no later than at time $t_2$, and in all reactors (3000-2, ..., 3000-*i*) in which the temperature is not lowered it is kept the same within a range of variation of ±2.0° C.

2. The process as claimed of claim 1, in which the temperature in the reactors of the reactor cascade 3000 increases, from reactor 3000-1 to reactor 3000-*i* in all states of operation (A, T, E).

3. The process of claim 1, in which it is always the case that
$T_{3000-1}$ is set to a value in the range from 25.0° C. to 65.0° C. and
the temperature in each of the reactors downstream in flow direction (3000-2, ..., 3000-*i***) is set to a value in the range from 35.0° C. to 200.0° C.

4. The process of claim 3, in which it is always the case that
$T_{3000-1}$ is set to a value in the range from 30.0° C. to 60.0° C. and
the temperature in each of the reactors downstream in flow direction (3000-2, ..., 3000-*i***) is set to a value in the range from 50.0° C. to 180.0° C.

5. The process of claim 1, in which the acidic catalyst (7) is a mineral acid.

6. The process of claim 1, in which step (B) further comprises:
(B-III) washing the organic phase (11) with washing liquid (13);
(B-IV) separating the mixture (14) obtained in step (B-III) into an organic phase (16) comprising di- and polyamines of the diphenylmethane series and an aqueous phase (15);
(B-V) distilling the organic phase (16) from step (B-IV) to obtain the di- and polyamines of the diphenylmethane series (18), with removal of a stream (17) comprising water and aniline.

7. The process of claim 6, additionally comprising:
(C) recycling stream (17), optionally after workup, into step (A-I) and/or, if the optional addition of further aniline (1) in step (A-II) is conducted, into step (A-II).

8. The process of claim 1, in which the molar ratio of total aniline used (1) to total formaldehyde used (2), n(1)/n(2), in all states of operation (A, T, E) is adjusted to a value of 1.6 to 20.

9. The process of claim 1, in which the process is operated during the transition state T such that the target values of n(1)/n(2), n(7)/n(1) for the end state E and the temperature in the first reactor 3000-1 of the reactor cascade 3000 exist at time $t_2$.

10. The process of claim 1, in which the temperature at each time $t_2$ in all reactors in the reactor cascade 3000 is maintained within a range of variation of ±2.0° C. for the duration of the production with the formaldehyde mass flow rate $m_2(E)$.

11. The process of claim 1, in which the period from $t_1$ to $t_2$ lasts from 1.00 minute to 120 minutes.

* * * * *